United States Patent [19]
Scofield et al.

[11] Patent Number: 5,719,064
[45] Date of Patent: Feb. 17, 1998

[54] PEPTIDE DIAGNOSTICS AND THERAPEUTICS FOR SPONDYLOARTHROPATHIES

[75] Inventors: R. Hal Scofield; John B. Harley, both of Oklahoma City, Okla.

[73] Assignee: Oklahoma Medical Research Foundation, Oklahoma City, Okla.

[21] Appl. No.: 944,143

[22] Filed: Aug. 31, 1992

[51] Int. Cl.$^6$ .................... G01N 33/543; C07K 14/195; C07K 14/74

[52] U.S. Cl. .................... 436/518; 436/544; 436/545; 436/546; 435/71; 530/324; 530/325; 530/326; 530/327; 530/328; 530/329

[58] Field of Search .................... 435/7.1; 530/324, 530/325, 326, 327, 328, 329, 300, 810, 868; 436/518, 544, 545, 546

[56] References Cited

U.S. PATENT DOCUMENTS

5,114,721  5/1992  Coher et al.

OTHER PUBLICATIONS

Bowie et al. Science 247:1306–1310 1990.
Harlow and Lane (ed) "Antibodies, A Laboratory Manual", published in 1988 by Cold Spring Harbor Laboratory (NY) see pp. 585–591.
Rock et al. PNAS 87:7517–21 1989.
Rose, "Manual of Clinical Laboratory Immunology" (Amer. Soc. Microbiol. 1986), pp. 99–109.
Parker, et al., "An HLA–A2/Beta$_2$–Microglobulin/Peptide Complex Assembled From Subunits Expressed Separately in *Escherichia coli*" *Molecular Immuno*. vol. 29, No. 3, pp. 371–378 (1992).
Parker, et al., "Peptide Binding to HLA–A2 and HLA–B27 Isolated from *Escherichia coli*", *J. Biol. Chem.*, vol. 267, No. 8, Mar. 15, 1992 (pp. 5451–5459).
Kumar et al. PNAS 87:1337–1341. Feb. 1990.
Tizard, Introduction to Vet. Immunology.
Bitar, D.M., et al., "Suppression of Experimental Autoimmune Encephalomyelitis by the Oral Administration of Myelin Basic Protein", *Cell Immunol*, 112:364–370, 1988.
Bodmer, J.G., et al., "Nomenclature for Factors of the HLA System, 1990", *Human Immunol*. 31:186–194, 1991.
Bodmer, J.G., et al., "HLA Class II Nucleotide Sequences, 1991", Human Immunol, 31:207–227, 1991.
Calin, A., et al., "Section VIII Spondyloarthropathies—Chapter 59 Ankylosing Spondylitis", eds. Textbook of Rheumatology, 3rd ed., Saunders: Philadelphia, pp. 1021–1037, 1989.
Calin, A., et al., "Demonstration of Shared Epitopes Between Bacterial Proteins and HLA Class–I Proteins Using Monoclonal Antibodies", *Scan J Rheum*, 87:S134–S139, 1990.
Cameron, et al., "Failure of *Klebsiella pneumoniae* Antibodies to Cross–react with Peripheral Blood Mononuclear Cells from Patients with Ankylosing Spondylitis", *Arthritis Rheum*, 30:300–305, 1987.

Cavender, D., et al., "Anti–HLA–B27 Antibodies in Sera from Patients with Gram–negative Bacterial Infections", *Arthritis Rheum*, 29:352–357, 1986.
Ceczy, et al., "A Factor(s) in *Klebsiella* Culture Filtrates Specifically Modifies an HLA–B27–associated Cell–surface Component", *Nature*, 283:782–784, 1980.
Devereux, J., et al., "A Comprehensive Set of Sequence Analysis Programs for the VAX", *Nuc Acid Res*, 12:387–395, 1984.
Duffaud, G.D., et al., "Expression and Secretion of Foreign Proteins in *Escherichia coli*", *Meth Immunol*. 153:492–507, 1992.
Ebringer, et al., in *HLA and Disease*, Dausset, J and Svejaard, J. eds. Inserm:Paris, p. 27, 1976. Not available. Will be forwarded shortly.
Ebringer, R.W., et al., "Sequential Studies in Ankylosing Spondylitis", *Ann Rheum Dis*, 37:146–151, 1978.
Ewing, C., et al., "Antibody Activity in Ankylosing Spondylitis Sera to Two Sites on HLA B27.1 at the MHC Groove Region (within Sequence 65–85), and to a *Klebsiella Pneumoniae* Nitrogenase Reductase Peptide (within Sequence 181–199)", *J Exp Med*, 171:1635–1647, 1987.
Hammer, R.E., et al., "Spontaneous Inflammatory Disease in Transgenic Rats Expressing HLA–B27 and Human β$_2$m: An Animal Model of HLA–B27–associated Human Disorders", *Cell*, 63:1099–1112, 1990.
Harley, J.B., et al., "Systemic Lupus Erythematosus: RNA–Protein Autoantigens, Models of Disease Heterogeneity, and Theories of Etiology", *J Clin Immunol*, 11:297–316, 1991.
Higgins, P.J., et al., "Suppression of Experimental Autoimmune Encephalomyelitis by Oral Administration of Mvelin Basic Protein and Its Fragments", *J. Immunol*, 140:440–445, 1988.
Jardetzky, T.S., et al., "Identification of Self Peptides Bound to Purified HLA–B27", *Nature*, 353:326–329, 1991.

(List continued on next page.)

*Primary Examiner*—Anthony C. Caputa
*Attorney, Agent, or Firm*—Arnall Golden & Gregory, LLP

[57] ABSTRACT

It has been determined that HLA B27 is related to proteins of the Gram negative enteric bacteria. The hypervariable regions of the HLA B alleles were compared to the known sequenced proteins for short consecutive amino acid identities. It was found that, unique to the HLA B alleles., HLA B27 shares an unexpected number of hexapeptides and pentapeptides with Gram negative bacteria proteins. The proteins from enteric organisms that share sequence with B27 tend to have sequences that satisfy protein sequence motifs which are thought to predict binding to B27. In addition, there is a sequence in B27, LRRYLENGK, which is predicted to bind as a peptide to B27. Binding of this peptide to B27 has been demonstrated. The disclosed peptides are useful for diagnostic and therapeutic purposes and can be used to design additional peptides from Gram negative enteric organisms can be identified to be important in the spondyloarthropathies. These peptides and their analogs can be used to screen for antibodies, and more importantly, T cells reactive with the peptides, which are indicative of the spondyloarthropathies.

7 Claims, No Drawings

OTHER PUBLICATIONS

Kahn, M.A., et al., "Ankylosing Spondylitis and Other Spondyloarthropathies", *Rheum Dis Clin North Amer,* 16:551–579, 1990.

Kinsella, T., et al., "Normal Anti–Klebsiella Lymphocytoxicity in Ankylosing Spondylitis", *Arthritis Rheum,* 29:358–362, 1986.

Lahesmaa, R., et al., "A Tetrapeptide Shared by Yersinia Outer Membrane Protein Yop1 and HLA–B27", *Scand J Rheum,* 88:S70–S71, 1990.

Madden, D.R., et al., "The Structure of HLA–B27 Reveals Nonamer Self–Peptide Bound in an Extended Conformation", *Nature,* 353:321–325, 1991.

Ogawasara, M., et al., "Mimicry of Human Histocompatibility HLA–B27 Antigens by *Klebsiella pneumoniae*", *Infect Immunol.* 51:901–908, 1986.

Ohno, S., "Many Peptide Fragments of Alien Antigens are Homologous with Host Proteins, Thus Canalizing T–Cell Responses", *Proc Natl Acad Sci USA,* 88:3065–3068, 1991.

Ohno, S., "How Cytotoxic T Cells Manage to Discriminate Nonself from Self at the Nonapeptide Level", Proc Natl Acad Sci USA, 89:4643–4647, 1992.

Schwimmbeck, P.L., et al., "Autoantibodies to HLA B27 in the Sera of HLA B27 Patients with Ankylosing Spondylitis and Reiter's Syndrome", *J Exp Med,* 166:173–181, 1987.

Scofield, R.H., et al., "Autoantigenicity of Ro/SSA Antigen is Related to a Nucleocapsid Protein of Vesicular Stomatitis Virus", *Proc Natl Acad Sci USA,* 88:3433, 1991.

Stieglitz, H., et al., "Identification of a 2–Md Plasmid from *Shigella flexneri* Associated with Reactive Arthritis", *Arthritis Rheum.* 32:937–946, 1992.

Terasaki, P.I., et al., "Regarding the Ankylosing Spondylitis/Klebsiella/HLA–B27 Problem", *Arthritis Rheum,* 30:353–354, 1987.

Tsuchiya, N., et al., "Antibodies to the Peptide from the Plasmid–coded Yersinia Outer Membrane Protein (YOP1) in Patients with Ankylosing Spondylitis", *Clin Exp Immunol,* 82:493–498, 1990.

Tsuchiya, N., et al., "Studies of Humoral and Cell–mediated Immunity to Peptides Shared by HLA–27.1 and *Klebsiella Pneumoniae* Nitrogenase in Ankylosing Spondylitis", *Clin Exp Immunol,* 76:354–360, 1989.

Wilbur, W.J., et al., "Rapid Similarity Searches of Nucleic Acid and Protein Data Banks", *Proc Natl Acad Sci USA,* 80:726–730, 1983.

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Yersinia ( x i ) SEQUENCE DESCRIPTION: SEQ ID NO:1:

Gln  Thr  Asp  Arg
    1

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Shigella flexneri ( x i ) SEQUENCE DESCRIPTION: SEQ ID NO:2:

Ala  Gln  Thr  Asp  Arg
    1                      5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:3:

Leu  Arg  Arg  Tyr  Leu  Glu  Asn  Gly  Lys
    1                      5

( 2 ) INFORMATION FOR SEQ ID NO:4:

( i ) SEQUENCE CHARACTERISTICS:
        ( A ) LENGTH: 9 amino acids (B) TYPE: amino acid
                    (C) STRANDEDNESS: single
                    (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:4:

Lys  Arg  Xaa  Xaa  Xaa  Xaa  Xaa  Xaa  Ala
        1                   5

(2) INFORMATION FOR SEQ ID NO:5:

(i) SEQUENCE CHARACTERISTICS:
                    (A) LENGTH: 9 amino acids
                    (B) TYPE: amino acid
                    (C) STRANDEDNESS: single
                    (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:5:

Lys  Arg  Xaa  Xaa  Xaa  Xaa  Xaa  Xaa  Leu
        1                   5

(2) INFORMATION FOR SEQ ID NO:6:

(i) SEQUENCE CHARACTERISTICS:
                    (A) LENGTH: 9 amino acids
                    (B) TYPE: amino acid
                    (C) STRANDEDNESS: single
                    (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:6:

Lys  Arg  Xaa  Xaa  Xaa  Xaa  Xaa  Xaa  Tyr
        1                   5

(2) INFORMATION FOR SEQ ID NO:7:

(i) SEQUENCE CHARACTERISTICS:
                    (A) LENGTH: 9 amino acids
                    (B) TYPE: amino acid
                    (C) STRANDEDNESS: single
                    (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:7:

```
Arg  Arg  Xaa  Xaa  Xaa  Xaa  Xaa  Xaa  Ala
1                 5
```

( 2 ) INFORMATION FOR SEQ ID NO:8:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: internal ( x i ) SEQUENCE DESCRIPTION: SEQ ID NO:8:

```
Arg  Arg  Xaa  Xaa  Xaa  Xaa  Xaa  Xaa  Leu
1                 5
```

( 2 ) INFORMATION FOR SEQ ID NO:9:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: internal ( x i ) SEQUENCE DESCRIPTION: SEQ ID NO:9:

```
Arg  Arg  Xaa  Xaa  Xaa  Xaa  Xaa  Xaa  Tyr
1                 5
```

( 2 ) INFORMATION FOR SEQ ID NO:10:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: internal ( x i ) SEQUENCE DESCRIPTION: SEQ ID NO:10:

```
Ala  Arg  Xaa  Xaa  Xaa  Xaa  Xaa  Xaa  Lys
1                 5
```

( 2 ) INFORMATION FOR SEQ ID NO:11:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:11:

Gly Arg Xaa Xaa Xaa Xaa Xaa Xaa Lys
1               5

(2) INFORMATION FOR SEQ ID NO:12:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:12:

Phe Arg Xaa Xaa Xaa Xaa Xaa Xaa Lys
1               5

(2) INFORMATION FOR SEQ ID NO:13:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:13:

Leu Arg Xaa Xaa Xaa Xaa Xaa Xaa Lys
1               5

(2) INFORMATION FOR SEQ ID NO:14:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Klebsiella pneumoniae (x i) SEQUENCE DESCRIPTION: SEQ ID NO:14:

Ala Lys Ala Gln Asn Thr
1               5

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Klebsiella pneumoniae ( x i ) SEQUENCE DESCRIPTION: SEQ ID NO:15:

```
Gln  Thr  Asp  Arg  Glu  Asp  Glu  Leu
 1                    5
```

( 2 ) INFORMATION FOR SEQ ID NO:16:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

```
Lys  Ala  Lys  Ala  Gln  Thr  Asp  Arg  Glu  Asp  Leu  Arg  Thr  Leu  Leu  Arg
 1                    5                        10                       15
```

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Salmonella typhimurium ( x i ) SEQUENCE DESCRIPTION: SEQ ID NO:17:

```
Asp  Leu  Arg  Thr  Leu  Leu
 1                    5
```

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Salmonella typhimurium ( x i ) SEQUENCE DESCRIPTION: SEQ ID NO:18:

```
Leu  Arg  Thr  Leu
1
```

( 2 ) INFORMATION FOR SEQ ID NO:19:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:19:

```
Gly  Pro  Asp  Gly  Arg  Leu  Leu  Arg  Gly  Tyr  His  Gln  Asp  Ala  Tyr  Gly
1                  5                            10                       15
```

( 2 ) INFORMATION FOR SEQ ID NO:20:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo sapiens ( x i ) SEQUENCE DESCRIPTION: SEQ ID NO:20:

```
Glu  Trp  Leu  Arg  Arg  Tyr  Leu  Glu  Asn  Gly  Lys  Glu  Thr  Leu  Gln  Arg
1                  5                            10                       15

Val  Asp  Pro  Pro  Lys
                    20
```

( 2 ) INFORMATION FOR SEQ ID NO:21:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Homo sapiens ( x i ) SEQUENCE DESCRIPTION: SEQ ID NO:21:

```
Glu Trp Leu Arg Arg Tyr Leu Glu Asn Gly Lys Glu Thr Leu Gln Arg
1               5                   10                  15
Val Asp Pro
```

( 2 ) INFORMATION FOR SEQ ID NO:22:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Pseudomonas aeruginosa ( x i ) SEQUENCE DESCRIPTION: SEQ ID NO:22:

```
Leu Pro Arg Leu Arg Arg Tyr Leu Glu Ala Arg Arg Asp Val Ile
1               5                   10                  15
```

( 2 ) INFORMATION FOR SEQ ID NO:23:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Klebsiella pneumoniae ( x i ) SEQUENCE DESCRIPTION: SEQ ID NO:23:

```
Asp Ile Glu Trp Leu Arg Arg Cys Val Glu Ala Phe Gly Leu Gln Pro
1               5                   10                  15
```

( 2 ) INFORMATION FOR SEQ ID NO:24:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (i v) ANTI-SENSE: NO (v) FRAGMENT TYPE: internal (v i) ORIGINAL SOURCE:
    (A) ORGANISM: E. coli (x i) SEQUENCE DESCRIPTION: SEQ ID NO:24:

```
Ala  Asp  Ala  Arg  Arg  Tyr  Leu  Glu  Trp  Gly  Ala  Thr  Phe  Val  Ala
1              5                        10                       15
```

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
        (A) ORGANISM: Bacillus megaterium (x i) SEQUENCE DESCRIPTION: SEQ ID NO:25:

```
Ala  Arg  Val  Thr  Ala  Arg  Arg  Tyr  Leu  Glu  Phe  Leu  Glu
1              5                        10
```

(2) INFORMATION FOR SEQ ID NO:26:

(i) SEQUENCE CHARACTERISTICS:
        (A) LENGTH: 15 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
        (A) ORGANISM: E. coli (x i) SEQUENCE DESCRIPTION: SEQ ID NO:26:

```
Thr  Gly  Ser  Tyr  Arg  Tyr  Ser  Asp  Asp  Asn  Gly  Lys  Glu  Thr  Gly
1              5                        10                       15
```

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS: single
        (D) TOPOLOGY: linear (i i) MOLECULE TYPE: peptide (i i i) HYPOTHETICAL: YES (i v) ANTI-SENSE: NO (v) FRAGMENT TYPE: internal (x i) SEQUENCE DESCRIPTION: SEQ ID NO:27:

Ala Arg Xaa Xaa Xaa Xaa Xaa Xaa Arg (2) INFORMATION FOR SEQ ID NO:28:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:28:

Gly Arg Xaa Xaa Xaa Xaa Xaa Xaa Arg (2) INFORMATION FOR SEQ ID NO:29:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:29:

Phe Arg Xaa Xaa Xaa Xaa Xaa Xaa Arg (2) INFORMATION FOR SEQ ID NO:30:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: internal (xi) SEQUENCE DESCRIPTION: SEQ ID NO:30:

Leu Arg Xaa Xaa Xaa Xaa Xaa Xaa Arg

PEPTIDE DIAGNOSTICS AND THERAPEUTICS FOR SPONDYLOARTHROPATHIES

BACKGROUND OF THE INVENTION

This invention is generally in the field of diagnostics and therapeutics for autoimmune disorders, in particular peptide-based technology for diagnosis and treatment of spondyloarthropathies.

Ankylosing spondylitis, Reiter's syndrome, and other reactive arthritides are referred to as spondyloarthtopathies. The spondyloarthropathies are arthritic disorders that share a characteristic inflammatory involvement of the spine. They include spondylitis associated with inflammatory bowel disease or psoriasis. The ligaments and tendons of the spine become inflamed, especially at the sites of their insertion into the bones of the vertebral column. The ligaments and tendons then calcify and the spine loses mobility, sometimes to the point of becoming completely rigid. Often the process is very painful. In many patients the loss of mobility of the back may be a serious handicap. Other organs, including the eyes, aorta, joints, heart, gastrointestinal tract, skin and genitourinary tract, may also be involved in patients. Uveitis associated with HLA B27 is also considered to be a spondyloarthropathy.

Ankylosing spondylytis is the prototype spondyloarthropathy and is the most common of these diseases, being clinically evident in about 0.2% of the adult caucasian Americans, as reported by M. A. Khan and S. M. van der Linden, Rheum. Dis. Clin. North Amer. 16:551–579 (1990). At least 300,000 Americans have one of the spondyloarthropathies. In ankylosing spondylytis, the disease often begins in the sacroiliac joints and ascends the spine. Many patients, and especially those who are manual laborers, are unable to continue gainful employment. These diseases cause great suffering, sometimes throughout adult life, and are the source of enormous economic hardship.

Up to ninety-five percent of the individuals with spondyloarthropathy have the B27 (or B*2705) Class I histocompatibility allele (HLA), as reviewed by Calin, A., Spondyloarthropathies, in Kelley, W N, Harris, E D, Ruddy, S, Sledge, C B, eds, Textbook of Rheumatology, 3rd ed., Saunders: Philadelphia, p. 1023–1039, 1989. Patients affected by spondyloarthropathy tend to harbor a variety of Gram negative enteric bacteria including Yersinia, Shigella, Salmonella, Campyiobacter, and Klebsiella (Calin; Rayborne, et al., Scand. J. Rheum. 87:S134–S139, 1990; Ebringer, et al., A. Ann. Rheum. Dis. 37:146–151, 1978.). Several lines of immunologic evidence have associated these bacteria with the spondyloarthropathies (Ogawasara, et al., Infect. Immunol. 51:901–908, 1986; Ebringer, et al., in HLA and Disease, Dausset, J and Svejaard, J, eds. INSERM:Paris, p.27. 1976; and Geczy, et al., Nature 283:782–784, 1980).

There has been some data implicating Klebsiella pneumoniae in the pathogenesis of spondyloarthropathy which includes crossreactivity of an anti-B27 monoclonal antibody with Klebsiella antigens. Immune associations between Klebsiella and ankylosing spondylitis have not been consistently found, however (Cameron, et al., Arthritis Rheum. 30:300–305, 1987; Kinsella, T, Fritzler, M, Lewkonta, R. Arthritis Rheum. 29:358–362, 1986; Terasaki, et al., Arthritis Rheum. 30:353–354, 1987; Cavender, et al., Arthritis Rheum. 29:352–357, 1986; Tsuchiya, et al., Clin. Exp. Immunol. 76:354–360, 1989). A possible structural explanation for the association of the spondyloarthropathies and Gram negative bacteria has been proposed, based upon the six consecutive amino acids, QTDRED (SEQ. ID NO: 15), shared between HLA B*2705 and Klebsiella pneumoniae nitrogenase reductase (Schwimmbeck, et al., J. Exp. Med. 166:173–181, 1987). Antibodies in the sera of some patients with ankylosing spondylitis bind the region of both B*2705 and the nitrogenase which contains the shared sequence (Schwimmbeck, et al. J. Exp. Med. 166:173–181, 1987; Ewing, et al., J. Exp. Med. 171:1635–1647, 1987).

Two other shorter sequences shared by B*2705 and Gram negative enterics associated with spondyloarthropathies have been identified subsequently. The Yersinia outer protein 1 (YOP1) shares four consecutive amino acids, QTDR (SEQ ID NO. 1) , with the first hypervariable region of B*2705 (Lahasmaa, et al., Scand. J. Rheum. 88:S70–S71, 1990). Shigella flexneri shares a pentapeptide, AQTDR (SEQ ID. NO. 1), with the first hypervariable region (Stieglitz, et al., Arthritis Rheum. 32:937–946 (1992)). These are also reputed to be antigenic for some spondyloarthropathy patient sera (Tsuchiya, et al., J. Clin. Invest. 86:1193–1203, 1990; Tsuchiya, et al., Clin. Exp. Immunol. 82:493–498, 1990). Additional support for this relationship is found in work reported utilizing rats transgenic for B27, reported by Hammer, et al., Cell 63:1099–1112 (1990).

While the data are interesting, there has been no clear demonstration of the etiologic agent or cause of ankylosing spondylitis, nor have diagnostic or therapeutic agents been developed which allow for the early diagnosis or treatment of this or related disorders, other than through the use of anti-inflammatories and immunosuppressants. Moreover, short sequences are commonly shared between otherwise apparently unrelated proteins (Ohno, S. Proc. Natl. Acad. Sci. (USA) 88:3065–3068, 1991; Harley, J B, Scofield, R H. J. Clin. Immunol. 11:297–316, 1991). For example, a seven of eight or better amino acid match between the 538 amino acid Ro/SSA peptide and the more than 12,476 protein sequences of the database (NBRF release 21, June 1989) was found for 9% of the octapeptides of the Ro/SSA amino acid sequence (Scofield, R. H., Harley J B. Proc. Natl. Acad. Sci. (USA) 88:3433, 1991). Also, Ohno has found that two evolutionarily unrelated proteins on average share two tetrapeptides and one pentapeptide per 500 residues (Ohno, Proc. Natl. Acad. Sci. 88:3065–3068). One is led to the conclusion that this sharing of primary structures occurs as a consequence of chance and of convergent evolutionary pressures leading to similar structural solutions. The structural similarity or even identity of individual short amino acid sequences does not necessarily provide insight into pathogenesis or etiology. The possible valid inferences are, therefore, limited when they are considered alone. It is much more powerful to apply controlled statistical tests to specific hypotheses as has been done in this invention.

It is therefore an object of the present invention to provide diagnostic and therapeutic agents for the spondyloarthropathies, and methods of use thereof.

It is a further object of the present invention to provide a mechanism for the development of spondyloarthropathies which allows the development of new therapeutic agents for the treatment of spondyloarthropathies.

SUMMARY OF THE INVENTION

It has been determined that HLA B*2705 is related to proteins of the Gram negative enteric bacteria. The hypervariable regions of the HLA B alleles were compared to the known sequenced proteins for short consecutive amino acid identities. It was found that, unique to the HLA B alleles, HLA B27 shared an unexpected number of hexapeptides and pentapeptides with Gram negative bacteria proteins.

In addition, application of a peptide sequence motif derived from the sequences of peptides binding B27 has produced two additional findings. First, the enteric organisms that share at least pentapeptide sequence with the B*2705 hypervariable regions also tend to have the B*2705 binding motif in close proximity to the shared sequence. Second, a sequence in B*2705, LRRYLENGK (SEQ ID. NO. 3), satisfies the motif. The enteric proteins that share sequence with this peptide are particularly likely to also have the B*2705 binding motif in or overlapping with LRRYLENGK (SEQ ID. NO. 3).

These results define special properties of B27 which are believed to be important in the pathogenesis of the spondyloarthropathies and any other B*2705 associated inflammatory disorder. In particular, peptides from enteric organisms which share sequence with B*2705 and which bind B*2705 and/or other HLA molecules are considered to be important in the genesis of the inflammatory response culminating in spondyloarthropathy. It is believed that the mechanism involves B*2705, peptides from enteric organisms and the T cell receptors that bind these peptides in conjunction with B27. The presence of LRRYLENGK in B*2705 suggests that ablation of self-tolerance is important which is reinforced by the sequences shared between this peptide and enteric organisms.

The peptides identified by application of this new method should be useful in diagnosis, prognosis, therapy and monitoring of therapeutic efficacy.

These peptides can be used to screen for antibodies and, more importantly, for T cells reactive with the peptides, which are indicative of the spondyloarthropathies. The peptides, without or in conjunction with B27 and β2 microglobulin, can be used to reintroduce tolerance by either binding these reactive T cells to remove them from the patient, or by being administered to the patient in a strategy designed to increase or to reinduce tolerance. The preferred peptides are those identified by binding to an HLA antigen. Peptides bound by HLA is in turn bound by the patient's T cells, which result in activation of the T cells as measured by the production of cytokines, the appearance of or change in specific cell surface markers or proliferation. The peptides can be administered alone or in combination with other therapies such as antibiotics specific for the eliciting Gram negative organism(s). The peptides may be monomeric or multimeric.

DETAILED DESCRIPTION OF THE INVENTION

The discovery of the relationship between specific pentapeptides and hexapeptides of B27, which is associated with spondyloarthropathies, and Gram negative bacteria suggest convergent evolution between HLA B27 and these proteins. It is concluded that the forces which account for this finding are likely to account for the powerful association of HLA B27 and the spondyloarthropathies.

A systematic search of the known protein sequences has been conducted and the relatedness of these sequences to the HLA B alleles determined. The data reveal that unique to this set of Class I molecules, HLA B*2705 shares short amino acid sequence with the Gram negative enteric bacteria. At the length of a hexapeptide, there were 10 proteins in the PIR database which had a common sequence with the three hypervariable regions of B*2705. Half of these proteins were from Gram negative bacteria. The remaining non-B27 HLA B alleles shared hexapeptides with Gram negative organisms no more commonly than expected by chance based on the number of proteins from Gram negative organisms, relative to the total number of proteins in the data bank.

This analysis has been extended to pentapeptides. Again, the hypervariable regions of B*2705 allele primary amino acid sequence continue to be related to the primary sequence of proteins from Gram negative bacteria. Forty-seven of 286 pentapeptide matches to B*2705 are from proteins of Gram negative bacteria. Again, this is significantly different from the composition of the PIR database and from the number of Gram negative organism protein matches to the other HLA B alleles. The other B27 alleles, including B*2701, B*2702, B*2703, and B*2704, also share pentapeptides with proteins from Gram negative organisms statistically more frequently than the other B alleles.

On average, over 80% of the hexapeptide sequences shared by B27 and enteric organisms as well as nearly 40% of pentapeptide or longer sequences are in excess of the proportion that would be expected by chance.

Of the proteins sharing a hexapeptide with HLA B*2705, the *Klebsiella pneumoniae* nitrogenase and the *Salmonella typhimurium* hystidyl-PO4 aminotransferase each also shares a tetrapeptide with the first hypervariable region. These tetrapeptides are found adjacent to the shared hexapeptides within the B27 hypervariable region but separated in the primary sequence of the bacterial protein, as shown below. None of the other proteins sharing a hexapeptide with the B27 hypervariable sequences also shares a second sequence of four amino acids or longer.

This information can be used to define peptides which are useful as diagnostics for people having HLA B27 who are predisposed to (as defined herein, or having) spondyloarthropathies, as well as treatments for the spondyloarthropathies.

Identification of Peptides sharing sequence with Enteric Bacterial Proteins and HLAB27 and characterized by the presence of the HLAB27 binding motif.

METHODS

Computer Searches. Sequences of the PIR protein sequence databank (release 27, December 1990) were rapidly scanned for short segments of identity to the sequence of HLA B*2705 (entry HLHUB2) using a FORTRAN program linked to the Genetics Computer Group (Devereaux, et al., *Nuc. Acid Res.* 12:387–385 (1984)) software package (version 6.2) operating on a VAX 8350 using existing programs.

These sequence databank searching programs were designed to uncover sequences related to a query sequence by divergent evolution. Therefore a modification to a Genetics Computer Group software module was required in order to demonstrate the occurrence of sequences possibly related to a query sequence by convergent evolution through conservation of short sequences. These programs were used to determine short consecutive amino acid matches, 4 to 6 amino acids in length, between the HLA alleles and the database proteins. No substitutions were allowed so that the matched sequences were required to be identical in amino acid composition. Peptide sequences related to the query sequence by divergent evolution will certainly have high numbers of short sequence identities relative to the other sequences of the databank which are unrelated by divergent evolution to the query sequence. Given that the goal was to find amino acid identity between HLA-B alleles and proteins not related to them by divergent evolution, the 3119 sequences of the immunoglobulin superfamily were eliminated from the search of 28,796 possible sequences of the PIR databank.

Using the algorithm of Wilbur and Lipman (*Proc. Natl. Acad. Sci.* (USA) 80:726–730 (1983)), the number of k-tuples (short sequences, of length 4–6 in this study) in common between the query and a given databank sequence were first determined as the raw score. Overlapping k-tuples were treated independently and not combined. For a k-tuple size of 4, a single match of length 5 between query and databank sequence contributes 2 to the raw score; a match of 6 would contribute 3, etc. Normalized scores are 100 times the raw score divided by the product of the length two sequences, and reflect the average number of common k-tuples per 100 amino acids. Random k-tuple matches are more likely to occur in comparisons between longer sequences.

Madden, et al., *Nature* 353:321–325 (1991) and Jardetzky, et al., *Nature* 353:321–325 (1991) recently determined the sequence of endogenous peptides found in the binding cleft of crystallized B27 and Ohno (*Proc. Natl. Acad. Sci. USA*, in press, 1992) expanded on these sequences to develop a B27 binding motif. The motif includes an invariant arginine in position 2 of a nonapeptide. The patterns queried were as follows: (K,R)RXaaXaaXaaXaaXaaXaa(A,L,Y) and (A,G,F,L)RXaaXaaXaaXaaXaaXaa(K,R), where Xaa is any amino acid (SEQ. ID. Nos. 4–13, and 27–30) This motif was sought in the enteric organism protein sequences in the positions that overlap the pentapeptides (or greater) matches with B*2705 by one or more amino acids using the existing Genetics Computer group (Devereaux, et al., *Nuc. Acid Res.* 12:387–385 (1984)). It was appreciated that B27 contains a nonapeptide sequence, LRRYLENGK (SEQ ID. NO. 3), which fits the motif at positions 168 to 176 within the third hypervariable region. This aspect of B27 structure was thought to be particularly important in pathogenesis and represented a previously unappreciated mechanism of disease.

Sequence Identity Extension. In some cases, the sequence identity found between the query and a databank sequence could be extended by allowing a gap or mismatch in one of the sequences. A simple rule was built into the Fortran software which modelled these observed extensions for each k-tuple match, and the total number of extended identities over all k-tuple matches for each sequence was tallied during the databank search. Significance for the extension of the identity was estimated using a Monte Carlo simulation where a repeated random alignment of the query and test sequences (without regard to any match) was tested using the simple extension rule. For each sequence, the total number of extensions from the Monte Carlo simulations was used to model a Poisson distribution to determine the significance of identity in a match of the extension for the k-tuple matches.

Statistics. The number of amino acid sequence identities found for B*2705 was compared to the composition of the database and to the number of identities found for other HLA B alleles by Chi square analysis of a two by two contingency table. Raw scores from databank searches using a k-tuple size of 4, 5, or 6 (tetra-, penta-, or hexapeptide) common to HLA B27 were fit to a Poisson distribution using the Statistical Analysis System 5.6 software package (SAS Institute, Inc. SAS User's Guide: Statistics, SAS Institute, INC., Cary, N.C., 1986). A sample size of 25,677 and sample means of 1.216, 0.077, and 0.005 for raw scores of searches using k-tuple of 4, 5, or 6 (respectively) were used to determine p-values for the significance of a given raw score.

Short Sequence Identity. Given how commonly short sequences are shared between unrelated proteins (Ohno, S. *Proc. Natl. Acad. Sci.* (USA) 88:3065–3068, 1991; Harley, J B, Scofield, R H. *J. Clin. Immunol.* 11:297–316, 1991), it was determined whether a general relationship of primary amino acid sequence exists between HLA B27 and the proteins of Gram negative bacteria. To that end, the PIR protein database (release 27) was searched for short sequence identity to HLA B27 and other HLA B alleles. Ten hexapeptide matches with the hypervariable regions of B*2705 have been found, as shown in Table 1. Five of these (50%) are from Gram negative enteric organisms. In contrast, only 2,581 of the 25,677 non-immunoglobulin super-family sequences (10.1%) in the PIR data base are from Gram negative enterics, as shown in Table 2. The tendency of proteins from Gram negative organisms to share hexapeptide sequence with the hypervariable regions of B*2705 is unexpected (p<0.002, Fisher's exact test).

TABLE 1

Proteins sharing at least 6 consecutive amino acids with the hypervariable regions (HV) of HLA B27.

| HV | PROTEIN | ORGANISM |
|---|---|---|
| 1 | Nitrogenase reductase | *Klebsiella pneumoniae* |
| 1 | Histidyl-PO$_4$ aminotransferase | *Salmonella typhimurium* |
| 3 | Site-specific methyltransferase | *Pseudomonas aeruginosa* |
| 3 | Lethal factor precursor | *Bacillus anthraces* |
| 3 | Glutamate synthetase | *Escherichia coli* |
| 1 | pinFl | *Agrobacterium* |
| 1 | T2 | Epstein-Barr virus |
| 1 | CurC | *Streptomyces curacoi* |
| 2 | pol polyprotein | Avian RE virus |
| 3 | Monophenol monooxygenase | Human melanoma cells |

Searches were performed so that every possible overlapping hexapeptide of the three hypervariable regions (HV) of HLA B*2705 (PIR access code hlhub2) was compared to every possible overlapping hexapeptide of each of the proteins within PIR database (release 27). Sequences which were part of the immunoglobulin superfamily were eliminated from the database, resulting in 25,677 sequences which were compared to HLA B*2705. The PIR access code for the proteins which had an hexapeptide shared with HLA B*2705 are in order from the table: nikbfp, xnebhc, xyps7a, jq0032, b29617, a32306, a24938, a33073, fovdar, and yrmsb6. *E. coli* glutamate synthetase (b29617) shares 8 consecutive amino acids with HLA B*2705 in, and adjacent to, the third hypervariable region.

TABLE 2

The number of six and five consecutive amino acid identities found among the HLA-B molecule hypervariable regions when compared to protein sequences contained in the database.

|  | HLA B27 | Other HLA-B |
|---|---|---|
|  | Hexapeptide Matches | |
| Gram Negative Bacteria (Total PIR = 2,581) | 5* | 23 |
| Other Organisms (Total PIR = 23,096) | 5 | 140 |

TABLE 2-continued

The number of six and five consecutive amino acid identities found among the HLA-B molecule hypervariable regions when compared to protein sequences contained in the database.

|  | HLA B27 | Other HLA-B |
|---|---|---|
|  | Pentapeptide Matches | |
| Gram Negative Bacteria | 47** | 492 |
| Other Organisms | 239 | 4823 |

*P = 0.01 comparing the number of shared hexapeptides for B27 with the number for the other HLA-B alleles by the Fisher's Exact test. Hexapeptides were partitioned according to whether or not the protein containing the hexapeptide was found in a Gram negative bacteria. The analogous comparison of B27 and the PIR sequences are less likely (p < 0.002).
**p = $10^{-9}$, $\chi^2$ = 69. Pentapeptide amino acid matches to the HLA B27 hypervariable regions were partitioned as were the pentapeptides.

Searches were performed as described in Table 1. The other HLA-B Molecules included in these searches are given here according to the 1990 WHO nomenclature and are as follows: B*0701, B*0702, B*0801, B*1301, B*1302, B*1401, B*1402, B*1501, B*1801, B*3501, B*3502, B*3701, B*3801, B*3901, B*4001, B*4002, B*4101, B*4201, B*4401, B*4402, B*4601, B*4701, B*4901, B*5101, B*5201, B*5301, B*5701, B*5801, and B*7801. B*3801 and B*3901 were excluded from the search because only partial sequences are available for these alleles. The HLA serologic specificity, previous nomenclature and sequences of the HLA-B alleles are described by Bodmer, et al., *Human Immunol.* 31:186–194 (1991); Marsh, S G E, Bodmer, J G. *Human Immunol.* 31:207–227 (1991).

The protein sequence database was also examined for hexapeptides shared with the hypervariable region sequences of HLA-B alleles other than HLA B27. Finding only 23 of 163 (14.1%) shared hexapeptides from Gram negative bacteria is not different from the composition (10.1%) of the PIR database (p>0.05), but is different when compared to B27 (p=0.01) (Table 2). Each HLA B allele was also examined individually and no allele, other than B27, had a propensity to share hexapeptides with Gram negative microorganisms.

The sequences from the database sharing a hexapeptide with the hypervariable regions of B*2705 were examined for additional shorter shared sequences. Two of the five Gram negative proteins were found to have other regions of shared sequence while none of the proteins from other organisms did so. Both the *Klebsiella pneumoniae* nitrogenase reductase and the *Salmonella typhimurium* histidyl-PO₄ aminotransferase shared a tetrapeptide with the first hypervariable region of B*2705 in addition to the hexapeptide sequence also shared with B*2705.

*Klebsiella pneumoniae* nitrogenase reductase and *Salmonella typhimurium* histadyl-PO₄ aminotransferase share a hexapeptide and a tetrapeptide with the first hypervariable region of HLAB*2705. As shown below, the Klebsiella sequence identities are given above while the Salmonella sequence identities are given below the B*2705 sequence. The residue number of the N terminal amino acid of each shared sequence is given. In the Klebsiella nitrogenase reductase protein the amino acids represented by a gap in the B*2705 sequence are represented by lower case letters.

| Klebsiella | 51-A K A Qn T |
|---|---|
|  | 188-Q T D R E De L |
| B*2705 | 105-K A K A Q T D R E D L R T L L R(SEQ ID NO.16) |
|  | 212-D L R T L L(SEQ ID NO:17) |
| Salmonella | 171-L R T L(SEQ ID NO. 18) |

Both the hexapeptide and the tetrapeptide sequence identity of B27 with Klebsiella nitrogenase could be extended by allowing a gap in the B27 sequence, as shown above. No other hexapeptide match could be extended in this manner. A set of simulation experiments was conducted to determine the frequency of such an extension occurring by chance. In one such simulation a random 13 amino acid portion of B*2705 was matched with a random hexapeptide and tetrapeptide from the nitrogenase reductase. The sequence areas adjacent to these pairings were then compared for gap or mismatch extensions. A second simulation experiment was performed where the 13 amino acid sequence of B*2705 encompassing the first hypervariable was used instead of a random sequence. The pairings were repeated 500 times and the number of extensions recorded for each pairing. An extension did not occur in either simulation, confirming that the results found with B*2705 and the Klebsiella nitrogenase reductase are extremely unlikely ($p<10^{-6}$).

At the pentapeptide level the number of shared peptides is much larger. There are 286 pentapeptide or longer matches with the hypervariable regions of B*2705 in the PIR database of which 47 (16.5%) are from Gram negative enterics. Relative to the PIR database this is unlikely to have occurred by chance (p<0.001). Also, compared to HLA B*0701, as an example of a typical HLA-B allele, where 28 of 308 (9.1%) pentapeptides shared with PIR sequences are from Gram negative enterics, the tendency of B*2705 to share pentapeptides with Gram negative enterics is unexpected (p=0.005). When searches for pentapeptide amino acid sequence identities were carried out for all the HLA B alleles, it was found that there were 5325 matches in the PIR database to the hypervariable regions. Among these were 492 (9.2%) from proteins of Gram negative enteric bacteria. This was not different than the representation of these proteins in the PIR, but was significantly different than that found for B*2705 ($p<10^{-6}$).

The hexapeptide and pentapeptide sequence identities found in the PIR database to the hypervariable regions (HV) of HLA B*2705 and Gram negative enteric organisms are presented below. The amino acid sequences of each HV is given on the center line while the residue position is given along the top and bottom. The access code for each protein from the database overlies its shared sequence with B27. The protein of origin for the shared hexapeptides are listed in order from left to right from the Gram negative sequences in Table 1. HV2 and 3 are extended to encompass additional amino acids shared by the octapeptide of b29617 and the hexapeptide of zpecp3. The protein sequences containing a pentapeptide identity with the hypervariable regions B*2705 are as follows: first hypervariable—jq0559, *E. coli* Plasmid RK2 KfrA protein; ju0135, *Acetobacter* sp. aldehyde dehydrogenase, deecpe, *E. coli* phosphoribosylaminoimidazole; s01424, *Frankia*. sp. nitrogenase; niavf, *Azobacter vinelandii* nitrogenase iron protein; a25103, *Azotobacter vinelandii* nitrogenase; a35405, *Azotobacter vinelandii* chroococcum nitrogenase; s08320, *Azotobacter vinelandii* nitrogenase; s10429, *Azotobacter chroococcum* nitrogenase iron protein; s11793, *Pseudomonas aeruginosa* Phosphate-specific porin P; syech, *E. coli* histidine tRNA ligase; f27733, *Azotobacter*

*vinelandii* protein 5; s11886 *E. coli* Fim D protein; qqecfj, *E. coli* pho requlon 26k protein, second hypervariable; zpecp3, *E. coli* penicillin-binding protein 3 precursor; a32354, *Bacillus subtillis* CTP synthasep; s09214, *Pseudomonas syringae* acetyltransferase; s00836, *E. coli* plasmid MccB17 mcbE protein; s06302, *E. coli* transposase; s00252, *E. coli* shikimate dehydrogenase; ju0380, *E. coli* sensor protein PhoQ; vzebpt, *Salmonella typhimurium* virulence membrane protein phoQ; s07355, *E. coli* ornithine carbamoyltransferase; s00302, *E. coli* sok protein; s08214, *Pseudomonas diminuta;* a34192, *E. coli* phosphoribosylformylglycunamidine synthase; syecpg, *E. coli* phosphoribosylformylglycunamidine synthase; nqeca, *E. coli* 1,4-alphaglucan branching enzyme, third hypervariable; s01840, *Klebsiella pneumoniae* nitrogenase molybdenum protein nifN; jq0612, *E. coli* hypothetical protein 168; js0383, *Bacillus megaterium* 26.2K protein; a33465, H. influenzae lic-1 phase/variation protein D; mmecof, *E. coli* outer membrane feaD protein precursor; s00920, *E. coli* site-specific methyltransferase; s09207, *E. coli* beta galactosidase; ncecxv, *E. coli* ex-odeoxyribonuclease; xuecag, *E. coli* glycerol-3-phosphate acyltransferase; s04021, *Shigella dysenteriae* shiga toxin A chain precursor; a28626, *Shigella dysenteriae* shiga toxin A precursor; xubph9, Bacteriophage H19B shiga-like toxin A chain precursor; a32360, Bacteriophage 933W shiga-like toxin II variant A chain precursor; s01032, *E. coli* bacteriophage 933W shiga-like toxin II chain A precursor. Other proteins include nikbfp, *Klebsiella pneumoniae* nitrogenase reductase; snebhc, *Salmonella typhimurium* histadyl-PO$_4$ aminotransferase; xyps7a, *Pseudomonas aeruginosa* site-specific methyltransferase; jq0032, *Bacillus anthraces* lethal factor precursor; b29616, *Escherichia coli* glutamate synthetase. The PIR access code is given prior to each sequence.

The sequences and their alignments are:

sequences in the pentapeptides shared between B*2705 and the other sequences in the modified PIR database. The statistical significance of the results is not meaningfully changed by removing these duplicates from consideration.

B27 Binding Motif. The available sequences of peptides binding to B27 have made it possible to develop peptide sequence motifs that may be predictive of binding as described above. Accordingly, the sequence motifs (K,R) RXaaXaaXaaXaaXaaXaa(A,L,Y) and (A,G,F,L) RXaaXaaXaaXaaXaaXaa(K,R) (SEQ. ID. Nos. 4–13, and 27–30) have been sought in the enteric proteins that share at least a pentapeptide sequence with B*2705 hypervariable regions, as shown above, and compared with the non-enteric sequences that share sequences in these same regions of B*2705. Only those motifs that overlap a shared sequence by at least one amino acid have been included in this analysis. The shared sequences from the gram negative enteric organisms are much more commonly found to overlap with one of these motifs than are the non-enteric proteins that share sequences with B*2705 ($\chi^2$>p<0.002).

The B27 molecule contains a nonapeptide, LRRYLENGK (SEQ ID. NO. 3) beginning at amino acid residue 168 that conforms to the requirements for binding to and presentation by B27 in conjunction with β-2 microglobulin as defined by the B27 peptide binding motif. Each protein within the database that had sequence identity at this site in B*2705 has been searched for a nonapeptide which fits the B27 binding motif and also overlaps the amino acid identity to B*2705. It was found that of Gram negative enteric organisms with a sequence match at B*2705 residues 168 to 176, six of seven had a nonapeptide consistent with binding by B27 which was at the site of the match to the B*2705 molecule. On the other hand, only 6 of 49 proteins not from Gram negative enteric organisms with short sequence similarity to B*2705 residues 168 to 176 also had a binding motif

| 68 HV1 83 | 105 HV2 12 | 166 HV3 184 |
|---|---|---|
| KAKAQTDREDLRTLLR(SEQ ID NO. 16) | GPDGRLLRGYHQDAYG(SEQ ID NO. 19) | EWLRRYLENGKETLQRVDPPK(SEQ ID NO. 20) |
| | | xyps7a |
| nikbfp | | jq0032 |
| xnebhc | | |
| jq0559 | -zpecp3 | b29617– |
| ju0135 | a32354 | s01840 |
| deecpe | s09214 | jq0612 |
| s01424 | s00836 | js0383 |
| niavg | s0632 | a33465 |
| a25103 | s00252 | mmecof |
| a35405 | ju0380 | s00920 |
| s08320 | vzebpt | s09207 |
| s10429 | s07355 | ncecxv |
| s11793 | s00302 | xuecag |
| syech | a28214 | s004021 |
| f27733 | a34192 | a28626 |
| s11886 | syecpg | xubph9 |
| qqecfj | nqeca | a32360 |
| | | s01032 |

The PIR database contains entries of some completely identical sequences. Sometimes, these are entries of the partial sequence. There are, however, no duplicate sequences contained among those with a hexapeptide match to B27. For the analysis shown above, the duplications of identical sequences with pentapeptide matches have been included. The three sets of duplicate sequences among the shared pentapeptides of the hypervariable regions of B*2705 and Gram negative organisms are as follows (identified by access code); niavf and a35405; a25103, s08320, and s10429; a34192 and syepg. There are 23 sets of duplicate sequence ($\chi^2$=19.6, p=0.0002). The sequences and the Gram negative organisms with both sequence identity and a binding motif are shown in Table 3. The motif in each protein is in bold and the sequence identity with B*2705 is underlined. The proteins are named by their access code. The protein and organism are as follows: xyps7A, *Pseudomonas aeruginosa* site specific methyltransferase (adenine specific); s01840, *Klebsiella pneumoniae* nitrogenase molybdenum protein nifN; jq0612, *E. coli* hypothetical protein 168; js0383, *Bacillus megaterium* 26.2 K protein; mmecof, *E. coli* outer membrane faeD protein precursor.

TABLE 3 proteins from enteric organisms hich share consecutive amino acid sequence with HLA B27 residues 168-176 and have the binding motif for HLA B27.

| | |
|---|---|
| B27 HV3 | E WL R R Y L E N GKE T L G R V D P(SEQ ID NO. 21) |
| XYPS7A | L P R <u>L R R Y L</u> E A R RD V I(SEQ ID NO. 22) |
| S01840 | D I E WL R RC V E A F GL Q P(SEQ ID NO. 23) |
| JQ0612 | A D A <u>R R Y L</u> E WG A T F V A(SEQ ID NO. 24) |
| JS0383 | A R V T A R R Y L E F L E(SEQ ID NO. 25) |
| MMECOF | T G S Y R Y S DD <u>N G K E</u> T G(SEQ ID NO. 26) |

Taken together, these findings demonstrate that convergent evolution has taken place between these organisms and the HLA B27 of man, and that spondyloarthropathies are an expression of the resulting immunoregulatory events that occur in B27 positive individuals. By structurally imitating critical molecular decision making machinery of the immune response, the subsequent immunologic interactions are modulated, leading to immune dysregulation and the consequent pathologic expression of disease.

These results also led to directly testing whether LRRYLENGK (SEQ ID. NO. 3) is bound by B27; the experiments of which are described under Example 1, below. This finding in addition to the association of shared sequences with the motif presented immediately above powerfully implicates the participation of specific subsets of T cells in this process, either via their specific T cell receptor or via a particular subclass of T cell receptors.

Within the context of current immunologic knowledge, these observations also lead to a possible scenario for the autoimmune pathogenesis of the spondyloarthropathies which requires the following steps. First, the host is tolerized to its own B27 molecule. Then the host is exposed to an enteric organism that partially imitates B27 such that the enteric antigen becomes immunogenic. Those enteric peptides that bind HLA antigens, and especially those that satisfy the requirements to bind B27, hold the potential of breaking tolerance to B27 sequences. Once tolerance to the self peptides of B27 is broken, then the requirements are met to establish a chronic inflammatory condition.

Selection of Peptides for use in Diagnostics or Treatment

The peptides suitable for use as a diagnostic or in the treatment of patients predisposed to spondyloarthropathies via autoimmune mechanisms are drawn from two sources. First are those wherein the peptide is between seven and one hundred amino acid residues in length, and has sequence identity with one of the HLA B27 hypervariable sequences (KAKAQTDREDLRTLLR (SEQ ID NO. 16), GPDGRLL-RGYHQDAYG (SEQ ID NO. 19), and EWLR-RYLENGKETLQRVDPPK (SEQ ID NO. 20)), which are shared with enteric bacterial proteins, and which bind HLA class I or II antigens. Second are those peptides whose sequence is taken from gram negative organisms at the regions that these sequences are shared with the B27 hypervariable region sequence and encompasses any contiguous flanking sequence that is predicted to or demonstrated to bind to an HLA antigen. In a preferred embodiment, the peptide shares at least three to five contiguous amino acids with B27, and, in the most preferred embodiment, contains the B27 binding motif and is bound by B27.

In the preferred embodiment, the peptides consist of between seven and 100 amino acids, and can be made synthetically, by cleavage of isolated bacterial proteins, or recombinately, by expression of partial sequences encoding the bacterial proteins. Techniques for production of peptides by all of these methods are known, as are the nucleotide or amino acid sequences for many suitable bacterial proteins.

Enteric bacteria are defined as those bacteria normally found in, or which are pathogenic via, the gastrointestinal tract, including the mouth and urinary tract. Examples include Acinetobacter, Bacteroides, Escherichia, Azotobacter, Shigella, Campylobacter, Salmonella, Proteus, Yersinia, Serratia, Pseudomonas, Klebsiella, Bacillus, Haemophylus, Enterobacter, Vibrio and Acetobacter. In the most preferred embodiment, the peptide shares at least five amino acids with a bacterial protein and with HLA B27. In addition to the possibility of there being multiple short sequences shared by B27 and Gram negative organisms, there may be other structural or functional properties shared by the proteins that share short sequences with B27. For example, in the existing database there are 20 shared sequences from $E.\ coli$, there are eight shared sequences from nitrogenases, there are five shared sequences from Shigella toxins and there are four shared sequences from methyl or acetyl transferases. $E.\ coli$ is, of course, an ubiquitous inhabitant of the human gut and its genome has been extensively sequenced. When $E.\ coli$ is removed from consideration a significant relationship of B*2705 with non-$E.\ coli$ enteric bacteria is maintained.

Use of Peptides in Diagnostic Assays.

The peptides disclosed herein can be used in combination in assays, such as the solid phase assay, to diagnose patients. Using a mixture of peptides may increase the efficiency and reliability of such assays, as compared with using a single autoantigen, or a single peptide.

The peptides can be used in solution or immobilized to a solid substrate, such as a gel suitable for affinity chromatography, or a multi-well plate, using standard techniques known to those skilled in the art.

To facilitate detection and quantitation, the peptides can be labelled using standard techniques, for use in routine assays, with radioactive, fluorescent, or enzyme labels.

In an example of a diagnostic procedure, peripheral blood is obtained from a patient suspected of being predisposed to, or having, a spondyloarthropathy. The patient may have been preliminarily screened for the presence of HLA B27. The sample, containing either or both antibodies and T cells, is then mixed with a peptide as described above, sharing sequence with enteric bacterial proteins and an HLA antigen, preferably B27, and preferably also containing an HLA binding motif and more preferably the B27 binding motif, and binding between the peptide (as used herein, to include single peptides or mixtures of peptides) and the antibodies or, more importantly, the T cells, determined.

The detection of activation in a defined population of cells is determined by proliferation, the synthesis of cytokines, a change in cell surface markers, a change in cell membrane permeability, a change in the concentration of a protein species or a change in other substances that mediate activation. Activation is triggered by particular peptides, as defined above, and differences between individuals will predict or identify those at risk for spondyloarthropathy, disease activity, prognosis or response to therapy.

Use of Peptides in Therapeutic Compositions and Methods

The peptides can be used therapeutically in combination with a pharmaceutically acceptable carrier. The peptides can be administered in a dosage effective to block interaction of T cells with HLA B27 by immunizing against T cell causing disease or as a vaccine to redirect the immune system, thereby, generating tolerance to particular peptide sequences. The inflammation and clinical manifestations of the spondyloarthropathy is consequently ameliorated.

Pharmaceutical carriers are known to those skilled in the art and include encapsulation of compounds for oral administration, for example, in an enteric coating or in combination with a binder such as stearate or lactose, or in solution. Acceptable solutions include sterile water, saline, and buffered solutions at physiological pH. Peptides used as vaccines can be administered orally, intramuscularly, intravenously or subcutaneously. Other compounds will be administered according to standard procedures used by those skilled in the art. As defined herein, a pharmaceutical carrier is usually inert by itself but may have biological activity. For example, a vaccine may consist of immunogenic peptides or proteins in combination with an adjuvant.

Alternatively, the peptides used for treatment might include peptides homologous to an identified binding sequence, having modifications in charge, size, or backbone. These peptides, either free or bound to a carrier, could be delivered to a patient in order to decrease the amount of circulating HLA B27 or T cells interactive with HLA B27, or T cells interactive with a particular peptide. In addition, knowledge of the cross-reacting peptides should be useful for re-induction of tolerance. By analogy with other well known experimental models of the immune response, the response can be suppressed and tolerance induced by treatment with peptide. Peptide therapy with the cross-reacting sequences may be a potential therapy in autoimmune diseases.

Peptides can be used to make agents for neutralizing T cells or immobilized on substrate in extracorporeal devices for specific removal of T cells interactive with peptide bound by HLA B27, using methodology known to those skilled in the art.

Formulations of these peptides (or of their analogs) have the potential to alter the inflammatory response in individuals affected with spondyloarthropathy. One way is to reinduce tolerance to self, and particularly to B27. Oral administration of peptide formulations is a mode of therapy that could achieve this goal and induce antigen-specific tolerance, using sequences that are shared between B27 and enteric proteins or their analogs.

The animal model of experimental allergic encephalomyelitis has certain parallels that offers the possibility of designing a therapeutic approach. In the ordinary model animals immunized with myelin basic protein develop experimental allergic encephalomyelitis. This disease has clearly been shown to be T cell dependent. In recent years it has become clear that only certain regions of the molecule foster encephalomyelitis. It has been shown that the oral administration of myelin basic protein or of fragments thereof have the capacity to reduce the severity of, and in some cases prevent, experimental encephalomyelitis (B. M. Bitar, C. C. Whitacre *Cell. Immunol.* 112:364–370 (1988) and P. J. Higgins, H. L. Weiner *J. Immunol.* 140:440–445 (1988)). Rats were fed 25 micrograms to 20 milligrams of myelin basic protein on various days before and after immunization with myelin basic protein.

This very wide range of dosages and schedules used in the experimental model suggests that a wide range of oral doses and schedules could be successful in the treatment of human spondyloarthropathy. Refinement of suitable dosages can be determined by persons of ordinary skill using no more than ordinary experimentation. For example, optimum dosage can be determined using serially diluted preparations of the active agents of the present invention in connection with a suitable testing procedure. Alternatively, a matrix of dosages and frequency of administration can be established and groups of experimental subjects can be assigned to each point on the matrix in order to determine the optimal conditions.

The optimal route of administration may vary according to the disease manifestations in individual patients. This could likewise be determined by experimentation by one with ordinary skill in the art and would include administration of the therapeutic agent orally, enterally (i.e., by tube feeding), intravenously, subcutaneously, intramuscularly, intranasally, intraperitoneally, intraarticularly, intraocularly (would include topical application and injection) or intrabronchially (as an aerosol).

One method for suppressing the clinical manifestations in a patient in need of treatment might be to administer to the patient an effective amount of a suppressive agent selected from the group consisting of (i) an autoantigen (i.e., the HLA B27 hypervariable region or a derived peptide, the region containing LRRYLENGK is currently preferred); (ii) a heteroantigen (i.e., an enteric protein sharing sequence with B27 or a peptide derived therefrom); (iii) an analog of the autoantigen or heteroantigen with specific immunosuppressive activity (i.e., bearing a statistically significant (p<0.05) relationship to the sequence of either the autoantigen or the autoantigen) or (iv) combinations of any of the foregoing with or without a pharmaceutical carrier.

The term "suppression" is intended to include prevention of the clinical manifestations or symptoms, as well as complete elimination or at least measurable attenuation of such manifestations and symptoms. To be an "effective amount" the amount of the suppressive agent should be sufficient to cause a measurable and preferably a statistically significant attenuation of at least one of the clinical symptoms associated with the disorder. In the case of uveitis this could include but not be limited to eye discomfort, acuity or inflammation. In the case of other spondyloarthropathies this could include but is not limited to back pain; occiput to wall distance; severity of arthritis; thoracic expansion; and finger tip to floor distance. Measures of inflammation may also be obtained from radionuclide scans, such as Gallium 57 scans; changes on X-ray, magnetic resonance imaging or computerized axial tomography.

Effective amounts of these therapeutics for maximum efficacy may require repeated doses, including multiple daily doses. The duration of therapy will depend upon whether the continued presence of the therapeutic is required to sustain the therapeutic effect or whether changes induced by the therapeutic will remit disease and not require further therapy until the patient experiences an exacerbation, recrudescence or return of disease manifestations. Again, these conclusions may be made after experimentation by one with ordinary skill in the art.

An aerosol route of administration of autoantigen or heteroantigen may be effective in treatment of disease in patients. This may have the advantage that a smaller dose of the therapeutic would be needed to suppress autoimmune (both cell-mediated and antibody-mediated) responses. As used herein the term "aerosol" refers to finely divided solid or liquid particles that may be created using a pressurized system such as a nebulizer. The liquid or solid source material contains autoantigens and/or autoimmune disease suppressive fragments and analogs thereof as defined herein.

Other methods for delivering a therapeutic intraorally, intranasally or intrabronchially, which is partially determined by the size and velocity of the particle, can also be used.

An advantage of the aerosol route may be not only that less of the therapeutic might be required, but also that degradation by gastric juices might be avoided. Also, absorption in the airways is different from other sites which may constitute an advantage.

The composition of an effective therapeutic may also be useful in conjunction with existing therapies. Antibiotics may be important to change the normal flora of gram negative enteric organisms or for other purposes that increase the effectiveness of the peptide-based therapeutics resulting from this invention. For the autoimmune disorders, spondyloarthropathies and B27-associated uveitis these include corticosteriods, nonsteroidal anti-inflammatory agents, antibiotics, cyclosporin, antimalarials, sulfasalazine and immunosuppressives such as methotrexate, azathioprine and cyclophosphamide. The usage and dosage of these agents is dictated by the particular clinical circumstance and is known by those skilled in the art. Two problems, however, often limit the capacity of these agents to influence the course of disease. First, they are nonspecific in the sense that they generally influence the operation of many bodily systems and do not have a special reason to be particularly effective in the disorders which are the subject of this invention. Second, their effectiveness is often limited by side-effects and toxicities which can, on occasion, be life-threatening. The new agents which are developed from this invention, on the other hand, will specifically address the particular molecular mechanism which is responsible for the development of the spondyloarthropathies, the B27-related uveitis and, perhaps, other autoimmune related autoimmune disorders. Less toxicity and limitations in application are, therefore, anticipated.

The present invention will be further understood by reference to the following non-limiting example.

EXAMPLE 1

Demonstration That a Peptide Derived from B*2705, LRRYLENGK, Binds to B*2705

Protein Expression Plasmids. The cloning plasmid pIN-III-ompA (Duffaud, et al. *Meth. Immunol.* 153:492–507, 1992) directs the expression of protein as periplasmic inclusion bodies. This vector containing an approximately 2000 kb insert representing the DNA coding for the extracellular portion of HLA B*2705 was used to express the 274 amino acid sequence of the extracellular portion of HLA B*2705. The *E. coli* strain XL1-blue was transformed with the B*2705 expressing plasmid using standard techniques. A plasmid miniprep was performed and the DNA coding for B*2705 was cut from the plasmid using the restriction enzymes BamHI and HindIII. A 0.8% agarose gel electrophoresis was then done to confirm the presence of the 2000 kb DNA fragment coding for B*2705.

Isolation of HLA B*2705 Protein. Transformed *E. coli* were inoculated into 1 liter of LB broth and grown to the point of logarithmic growth. The samples were then centrifuged in a Sorvall RC5C rotor at 4870 rpm. The supernatant was discarded and the pellet resuspended in 10 ml of 23% sucrose/10 mM Tris chloride (pH 8.0) plus 0.2 ml of 5 mg/ml lysozyme and then diluted into 20 ml of ice cold 3 mM EDTA. This mixture was then passed through a French Press three times at a pressure of 10,000 psi. The material from the French Press was layered onto 5 ml of 67% sucrose/10 mM Tris (pH 8.0)/1 mM EDTA and centrifuged at 25,000 rpm for 1 hour in a Beckman LS-80 ultracentrifuge. The material remaining above the 67% sucrose layer was then placed on a 67%/53%/40% sucrose gradient (in 10 mM Tris (pH 8.0)/1 mM EDTA) and centrifuged for 18 hours as above. Each gradient layer was isolated and stored at 4° C. A 12.5% polyacrylamide gel electrophoresis was used to analyze each fraction after silver staining.

Peptide Synthesis. Peptides of nine amino acids in length were used for HLA B*2705 binding studies and were synthesized by standard methods.

HLA/β-2 Microglobulin/Peptide Complex Formation. Fifty μl of purified B*2705 (from the layer between the 67% and 53% gradient) was added to 450 μl of 10 mM 4-morpholineethanesulfonic acid (MES, pH 6.5)/150 mM NaCl and microcentrifuged for 15 minutes. The resulting pellet was resuspended in 12.5 μl of 8.8 M urea/125 mM MES (pH 6.5) with 2.5 μl of a 400 μM solution of peptide in 8.8 M urea/125 mM MES. This solution was incubated for 90 minutes at room temperature. Finally, 45 μl of 3.83 μM β-2 microglobulin in 10 mM MES/150 mM NaCl was added and allowed to incubate at 4° C. for 18 hours.

RESULTS

Agarose gel electrophoresis confirmed that the plasmid contained a 2000 kb insert consistent with the size expected of the B*2705 DNA. SDS-PAGE of the sucrose gradient fractions showed that the fraction at the interface of the 67% and 53% solution contained a 30,000 molecular weight band corresponding to the known molecular weight of the 274 amino acid extracellular portion of B*2705 without contamination. Other fractions also contained lesser amounts of this band contaminated with other molecular weight species.

Ability of B*2705 to bind a given peptide was determined by HPLC as described above. Control experiments with either no peptide or a peptide known to not be bound by B*2705 showed peaks of approximately 11,000 and 30,000 molecular weights, the respective expected size of β2 microglobulin and B*2705. Experiments utilizing an influenza peptide known to be a B*2705 restricted T cell epitope and therefore bound by B*2705 showed a peak of approximately 42,000 molecular weight. This is the size expected from the complex of peptide, B*2705 and β2 microglobulin. When the peptide corresponding to amino acid residues 168–176 of B*2705 (which conforms to the B*2705 binding motif) was used, then a complex at 42,000 Daltons was again observed. This set of experiments established that the peptide from within the B*2705 sequence predicted to bind B*2705, does in fact bind B*2705.

Modifications and variations of the compositions and methods for the diagnosis and treatment of spondyloarthropathies will be obvious to those skilled in the art from the foregoing detailed description. Such modifications and variations are intended to come within the scope of the appended claims.

---

We claim:

1. An isolated peptide of less than one hundred amino acid residues comprising a first contiguous peptide sequence of five amino acids which is present in a gram negative bacterial protein and a hypervariable region of HLA B27, and a second contiguous peptide sequence of a B27 binding motif which binds B27, the motif consisting of a contiguous sequence selected from the group consisting of KRXaaXaaXaaXaaXaaXaaA (SEQ. ID. No. 4), KRXaaXaaXaaXaaXaaXaaL (SEQ. ID. No. 5), KRXaaXaaXaaXaaXaaXaaY (SEQ. ID. No. 6), RRXaaXaaXaaXaaXaaXaaA (SEQ. ID. No. 7), RRXaaXaaXaaXaaXaaL (SEQ. ID. No. 8), RRXaaXaaXaaXaaXaaXaaY (SEQ. ID. No. 9), ARXaaXaaXaaXaaXaaK (SEQ. ID. No. 10), ARXaaXaaXaaXaaXaaR (SEQ. ID. No. 27), GRXaaXaaXaaXaaXaaXaaK (SEQ. ID. No. 11), GRXaaXaaXaaXaaXaaXaaR (SEQ. ID. No. 28), FRXaaXaaXaaXaaXaaXaaK (SEQ. ID. No. 12), FRXaaXaaXaaXaaXaaXaaR (SEQ. ID. No. 29), LRXaaXaaXaaXaaXaaK (SEQ. ID. No. 13), and LRXaaXaaXaaXaaXaaXaaR (SEQ. ID. No. 30), where Xaa is any amino acid, and wherein said motif is shared between HLA B27 and the gram negative bacterial protein.

2. The peptide of claim 1 wherein the first contiguous peptide shares at least five contiguous amino acids with B*2705.

3. The peptide of claim 1 wherein the first contiguous peptide shares at least five contiguous amino acids with the HLA B27 hypervariable regions selected from the group consisting of KAKAQTDREDLRTLLR (SEQ. ID No. 16), GPDGRLLRGYHQDAYG (SEQ. ID No. 19), and EWLRRYLENGKETLQRVDPPK (SEQ. ID No. 20).

4. A composition comprising the peptide of claim 1 in combination with an HLA molecule and β2 microglobulin wherein the β2 microglobulin is selected from the group consisting of isolated β2 microglobulin, β2 microglobulin in serum, and β2 microglobulin on cells or cell extracts.

5. The peptide of claim 1 immobilized on a substrate suitable for binding of T cell bearing a receptor immunoreactive with the peptide.

6. The peptide of claim 1 wherein the peptide is labelled with a label selected from the group consisting of fluorescent labels, radioactive labels, colorimetric labels, and enzyme labels.

7. The peptide of claim 1 wherein the first contiguous peptide has sequence identity with a contiguous five amino acid sequence in a protein selected from the group consisting of snebhc, *Salmonella typhimurium* histadyl-$PO_4$ aminotransferase; xyps7a, *Pseudomonas aeruginosa* site-specific methyltransferase; jq0032, *Bacillus anthraces* lethal factor precursor; b29616, *Escherichia coli* glutamate synthetase; jq0559, *E. coli* Plasmid RK2 KfrA protein; ju0135, Acetobacter sp. aldehyde dehydrogenase, deecpe, *E. coli* phosphoribosylaminoimidazole; s01424, Frankia. SP- nitrogenase; niavf, *Azobacter vinelandii* nitrogenase iron protein; a25103, *Azotobacter chroococcum* nitrogenase; a35405, *Azotobacter vinelandii* nitrogenase; s08320, *Azotobacter vinelandii* nitrogenase; s10429, *Azotobacter chroococcum* nitrogenase iron protein; s11793, *Pseudomonas aeruginosa* Phosphate-specific porin P; syech, *E. coli* histidine tRNA ligase; f27733, *Azotobacter vinelandii* protein 5; s11886 *E. coli* Fim D protein; qqecfj, *E. coli* pho regulon 26k protein; zpecp3, *E. coli* penicillin-binding protein 3 precursor; a32354, *Bacillus subtillis* CTP synthasep; s09214, pseudomonas syringae acetyltransferase; s00836, *E. coli* plasmid MccB17 mcbE protein; s06302, *E. coli* transposase; s00252, *E. coli* shikimate dehydrogenase; ju0380, *E. coli* sensor protein PhoQ; vzebpt, *Salmonella typhimurium* virulence membrane protein phoQ; s07355, *E. coli* ornithine carbamylase; s00302, *E. coli* sok protein; s08214, *Pseudomonas diminuta;* a34192, *E. coli* phosphoribosylformylglycunamidine; syegp, *E. coli* phosphoribosylformylglycunamidine; nqeca, *E. coli* 1,4-alphaglucan branching enzyme; s01840, *Klebsiella pneumoniae* nitrogenase molybdenum-iron protein nifN; jq0612, *E. coli* hypothetical protein 168; js0383, *Bacillus megaterium* 26.2K protein; a33465, *H. influenzae* lic-1 phase/variation protein D; mmecof, *E. coli* outer membrane feaD protein precursor; s00920, *E. coli* site-specific methyltransferase; s09207, *E. coli* beta galactosidase; ncecxv, *E. coli* ex-odeoxyribonuclease; xuecag, *E. coli* glycerol-3-phosphate acyltransferase; s04021, *Shigella dysenteriae* shiga toxin A chain precursor; a28626, *Shigella dysenteriae* shiga toxin A precursor; xubph9, Bacteriophage H19B shiga-like toxin A chain precursor; a32360, Bacteriophage 933W shiga-like toxin II variant A chain precursor; s01032, *E. coli* bacteriophage 933W shiga-like toxin II chain A precursor.

* * * * *